(12) United States Patent
Takada

(10) Patent No.: US 6,537,206 B2
(45) Date of Patent: Mar. 25, 2003

(54) SELF-PROPELLED COLONOSCOPE

(76) Inventor: Masazumi Takada, 622-26 Takatsukashinden, Matsudo-city, Chiba, 270-2222 (JP)

( * ) Notice: Subject to any disclaimer, the term of this patent is extended or adjusted under 35 U.S.C. 154(b) by 0 days.

(21) Appl. No.: 09/846,313

(22) Filed: May 2, 2001

(65) Prior Publication Data

US 2002/0049365 A1 Apr. 25, 2002

(30) Foreign Application Priority Data

Oct. 23, 2000 (JP) ........................................ 2000-322215

(51) Int. Cl.[7] ................................................ A61B 1/00
(52) U.S. Cl. ........................ 600/114; 600/101; 600/152
(58) Field of Search ............................... 600/101, 114, 600/122, 139, 155, 152; 604/271

(56) References Cited

U.S. PATENT DOCUMENTS 5,562,601 A * 10/1996 Takada ........................ 600/114
6,071,234 A * 6/2000 Takada ........................ 600/114
6,224,544 B1 * 5/2001 Takada ........................ 600/114

FOREIGN PATENT DOCUMENTS

| JP | 8-38416 | 2/1996 |
| JP | 2000-135199 | 5/2000 |
| JP | 2000-225092 | 8/2000 |

* cited by examiner

Primary Examiner—Tu Ba Hoang
(74) Attorney, Agent, or Firm—Young & Thompson

(57) ABSTRACT

A self-propelled colonoscope (1) includes an insertion tube (5) having a distal section (11), a bending section (13) and a flexible section (15), an operation unit (7) and driving unit. A plurality of endless belts (17) are arranged at the surface of the flexible section (15). Each endless belt (17) passes out to the surface of the flexible section (15) through a guide hole near the tip of the flexible section (15) by driving a driving unit mounted at a driving casing. The colonoscope is self-propelled into the colon by driving the endless belt (17). A length of the endless belt is 102 to 104% of the length of such as endless belt, when the endless belt tensely turns around, from the guide hole near the tip of the flexible section to the same hole, through the driving unit, while the flexible section (15) is maintained straight.

4 Claims, 6 Drawing Sheets

SELF-PROPELLED COLONOSCOPE

BACKGROUND OF THE INVENTION

1. Field of the Invention

The present invention relates to a self-propelled colonoscope, which does not cause pain to a patient during a colonoscopic examination for the colon.

2. Description of the Related Art

Colonoscopic examination is currently carried out by inserting a colonoscope by hand, so the examination may cause pain to a patient by excessively extending or bending the colon.

FIG. 6 is a drawing schematically showing an insertion path of a conventional colonoscope.

The tip of insertion tube 100 of the colonoscope is inserted from the anus 101 into the colon 103 and advances from the sigmoid colon 105 to the ileum 113, by passing through the descending colon 107, a transverse colon 109 and an ascending colon 111. The tip of the insertion tube 100 may be inserted until it reaches the distal end of the colon 103 (A) or it may be inserted into the ileum 113 for about 25 cm (B).

As shown in FIG. 6, the sigmoid colon 105, positioned near the insertion point of the colonoscope, is sharply bent in an S-shape. As a consequence, considerable operator skill is necessary to pass the insertion tube 100 through this portion. Further, the procedure causes increased pain to the patient.

And, the diameter of the insertion tube of a colonoscope conventionally used is 11.3 to 14.2 mm in general. When the tip of the colonoscope advances into the colon while bending, as shown in FIG. 6, the inner circle length and the outer circle length of the inserted bending insertion tube are different. So, in order to make the insertion tube advance steadily adjusting to the bend of the colon, a length of the inserting tube needs to have an allowance corresponding to the difference between the lengths of the inner circle and the outer circle of the inserted insertion tube while the insertion tube is bending.

SUMMARY OF THE INVENTION

In view of the above problems, it is an object of the present invention to provide a colonoscope which causes less pain to a patient and is able to be stably inserted.

According to an aspect of the present invention, a colonoscope is provided with a insertion tube comprising a distal section, a bending section and a flexible section, a lattice of a fiber of an image sensor element or an image-guide and a lattice of a fiber of a light-guide at the above-mentioned distal section, and an endless belt, which is sent out to the surface of the above-mentioned flexible section, from a guide hole near the tip of the flexible section, by driving a driving unit mounted at a driving unit casing, and reaches the same guide hole again through the above-mentioned driving unit, the endless belt being arranged on the surface of the above-mentioned flexible section, whereby the colonoscope is self-propelled into a colon by driving the endless belt. The length of said endless belt is 102 to 104% of a length such endless belt would be if it were tensely held at one end by the guide hole near the tip of said flexible section and at another end by the above-mentioned driving unit, while the flexible section was held straight.

On the surface of the flexible section, the endless belt, which passes out to the surface of said flexible section from the guide hole near the tip of said flexible section and returns to the driving unit, is driven by the driving unit, mounted at the driving unit casing, so that friction between the endless belt and an inner surface of the colon is able to make the colonoscope self-propelled. Since the colonoscope is self-propelled and adjusted to the shape of a colon, the colon is not extended or bent excessively, so that less pain is inflicted upon the patient.

On the other hand, the distal section of the insertion tube of the colonoscope inserted into the colon advances while adjusting to bent shapes of each part of the colon from the sigmoid colon to the ileum, through the descending colon, the transverse colon and the ascending colon. The diameter of the flexible section is 11.3 to 14.2 mm in general. Thus, when the tip of the insertion tube advances into the colon while bending, the inner circle length and the outer circle length of the inserted insertion tube are different. When the tip of the insertion tube reaches the ileum, the insertion tube will turn around, so that if the diameter of the insertion tube is 11.3 mm, the outer circle length of the tube is 2.2% longer than the straight length of the tube, and if the diameter is 14.2 mm, it is 2.77% longer. In the case of a self-propelled colonoscope in the present invention, the optimum diameter of the insertion tube is 16 mm so that the outer circle length is 3.12% longer.

Thus, it is necessary to set the length of the endless belt, arranged on the surface of the insertion tube, to have allowances corresponding to such differences. The length of the endless belt is 102 to 104% of the length of the endless belt, when the endless belt tensely turns around, from the guide hole near the tip of the flexible section of the insertion tube to the same guide hole, through the driving unit, while the insertion tube is maintained straight. So, the endless belt can sufficiently follow the bend of the insertion tube to be able to advance the colonoscope into the colon stably.

DESCRIPTION OF THE PREFERRED EMBODIMENT

Referring to the attached drawings, details of the embodiments of the present invention will be set forth.

Figure 1:
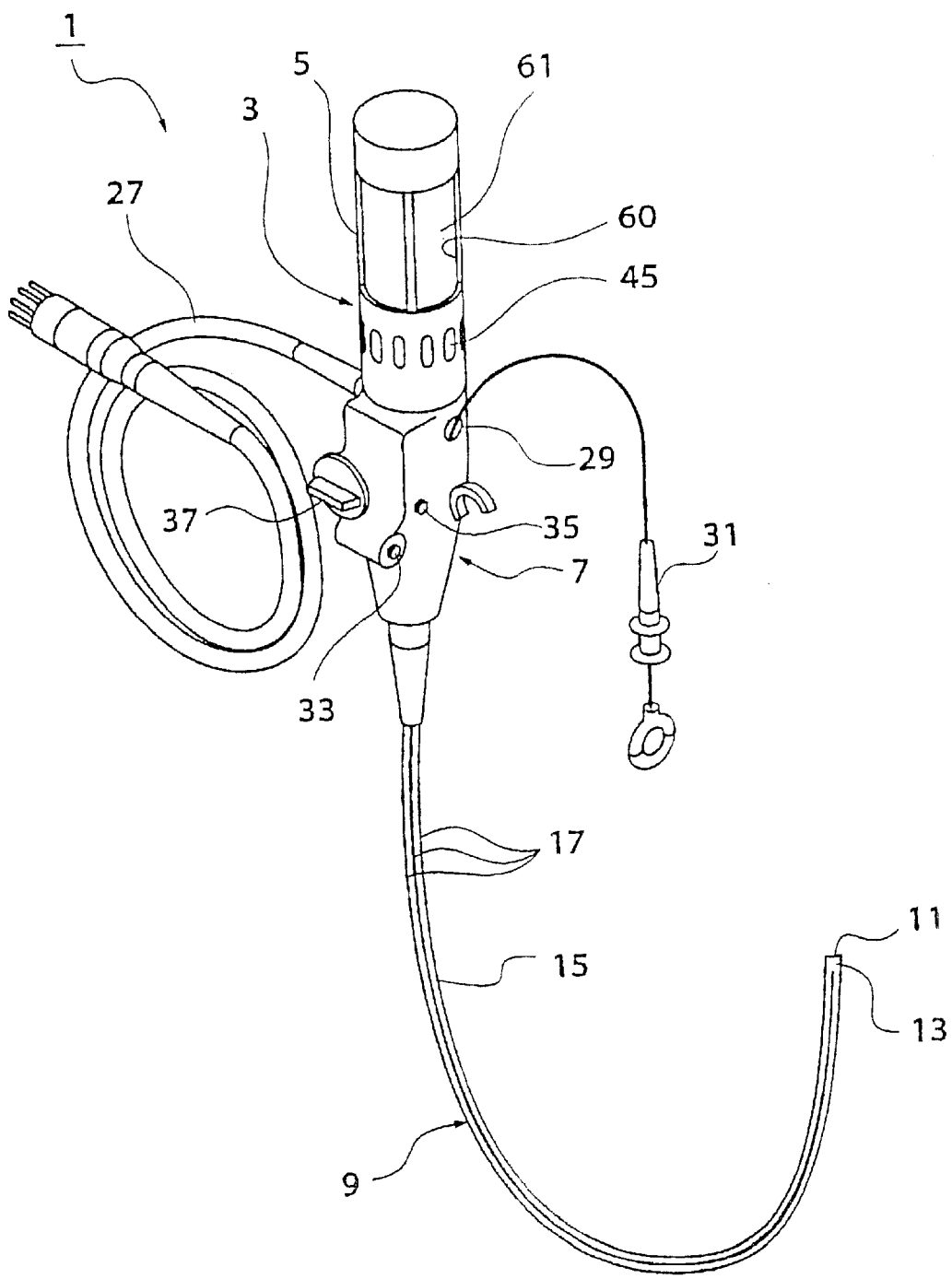
FIG. 1 shows a perspective view of the self-propelled colonoscope according to one embodiment of the present invention.

FIG. 1 shows a perspective view of the self-propelled colonoscope according to one embodiment of the present invention.

A self-propelled colonoscope 1 is provided with a belt driving unit 5 covered with a driving unit casing 3 at its upper part, an operation unit 7 under the belt driving unit, and an insertion tube 9 extending from the operation unit 7. The insertion tube 9 comprise a distal section 11, a bending section 13, and a flexible section 15. A plurality of endless belts 17 are longitudinally arranged on a surface of the flexible section 15.

Figure 2:
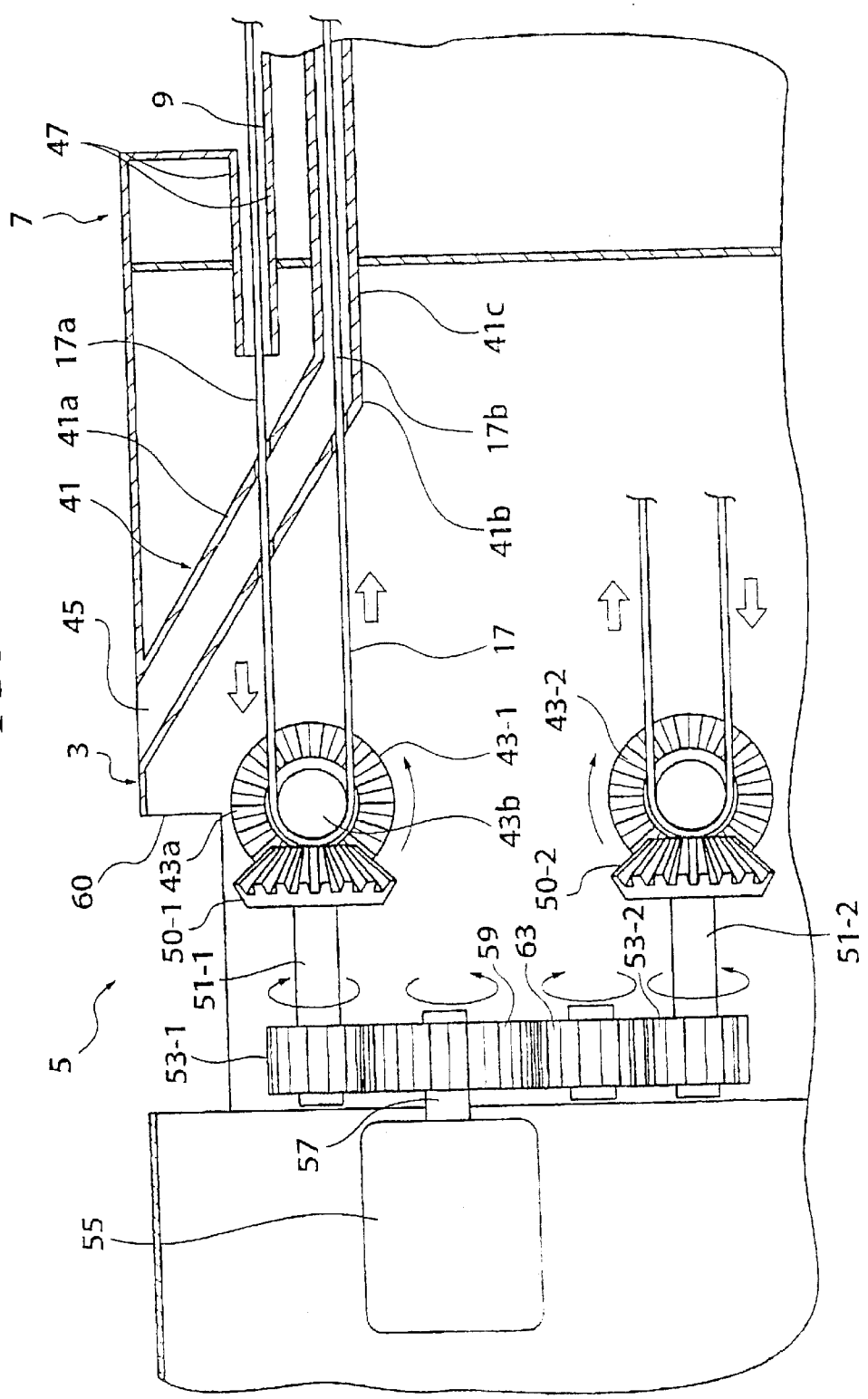
FIG. 2 shows a side sectional view of the driving unit of the colonoscope according to the invention.

FIG. 2 shows a side sectional view of the driving unit of the colonoscope according to the invention.

Figure 3:
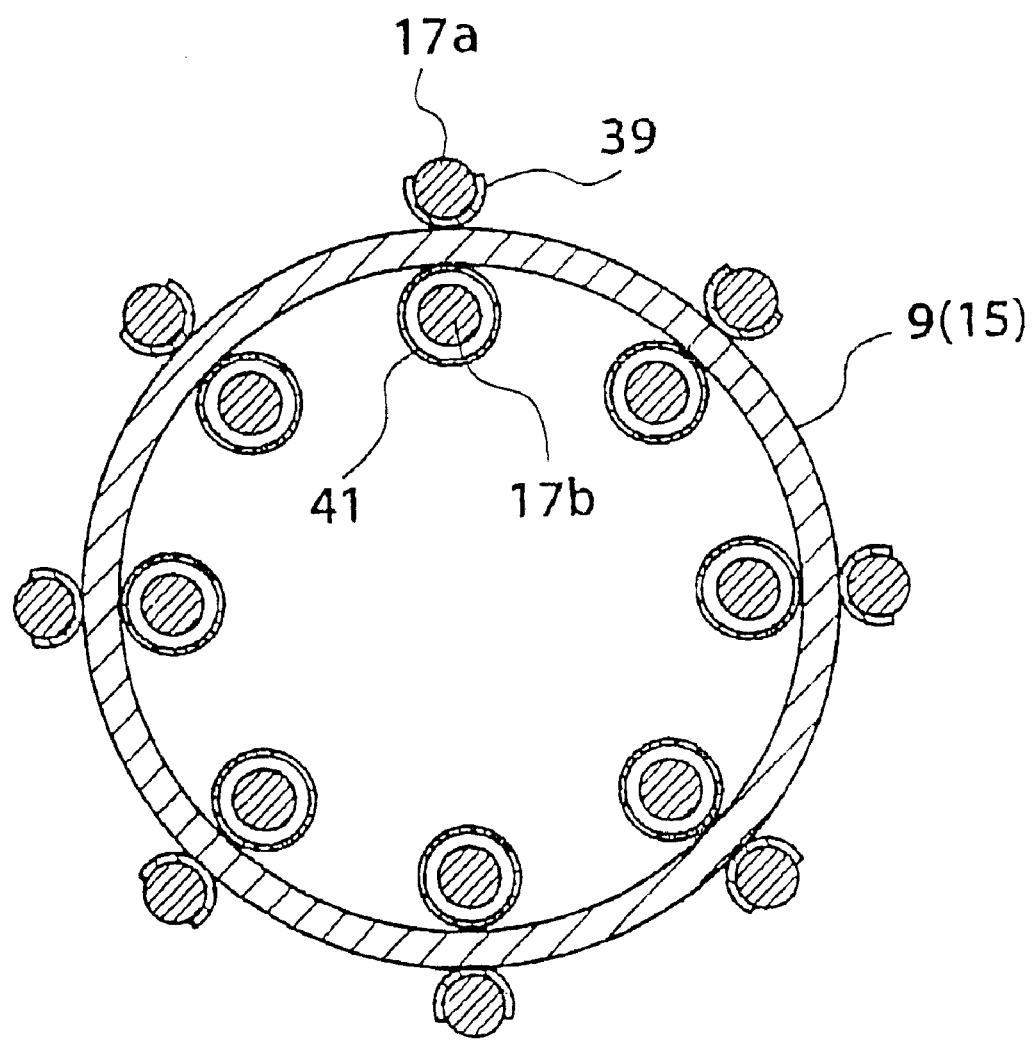
FIG. 3 shows a sectional view of the flexible section of the insertion tube of the colonoscope according to the invention.

FIG. 3 shows a sectional view of the flexible section of the insertion tube of the colonoscope according to the invention.

Figure 4:
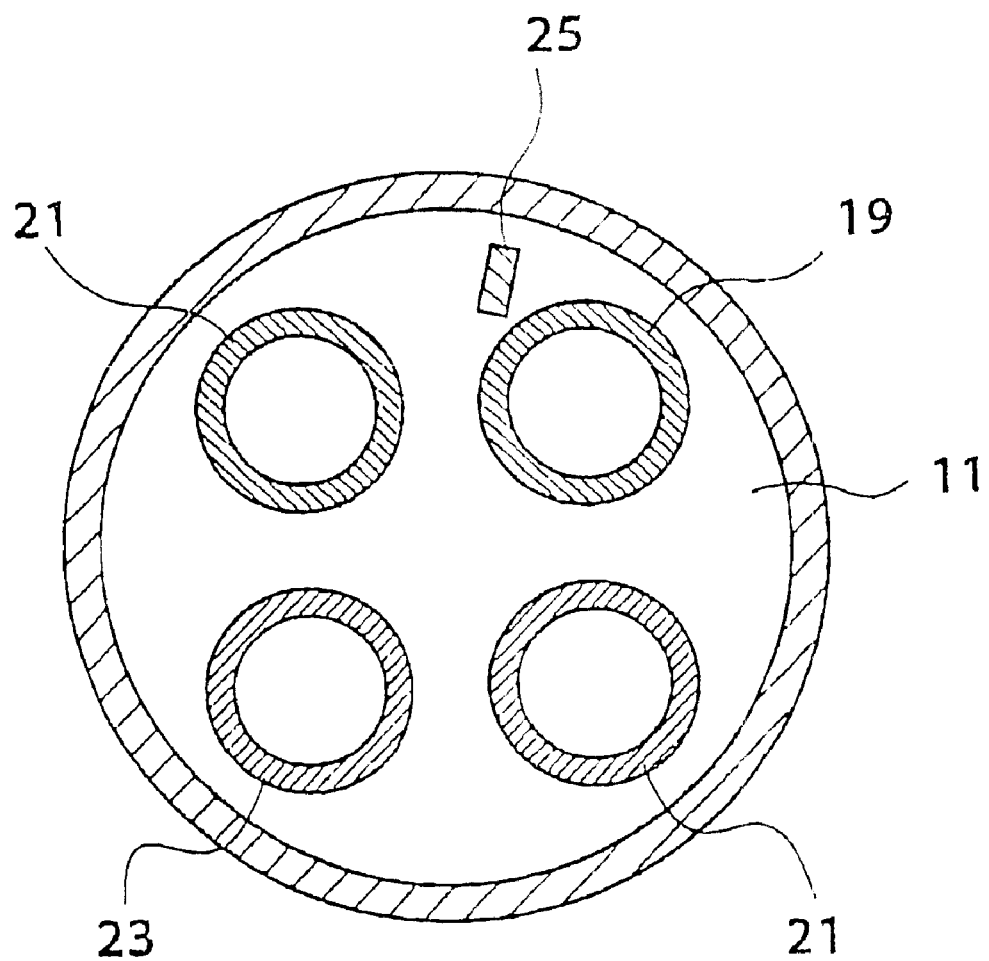
FIG. 4 shows a front view of the distal section of the insertion tube of the colonoscope according to the invention.

FIG. 4 shows a front view of the distal section of the insertion tube of the colonoscope according to the invention.

Figure 5:
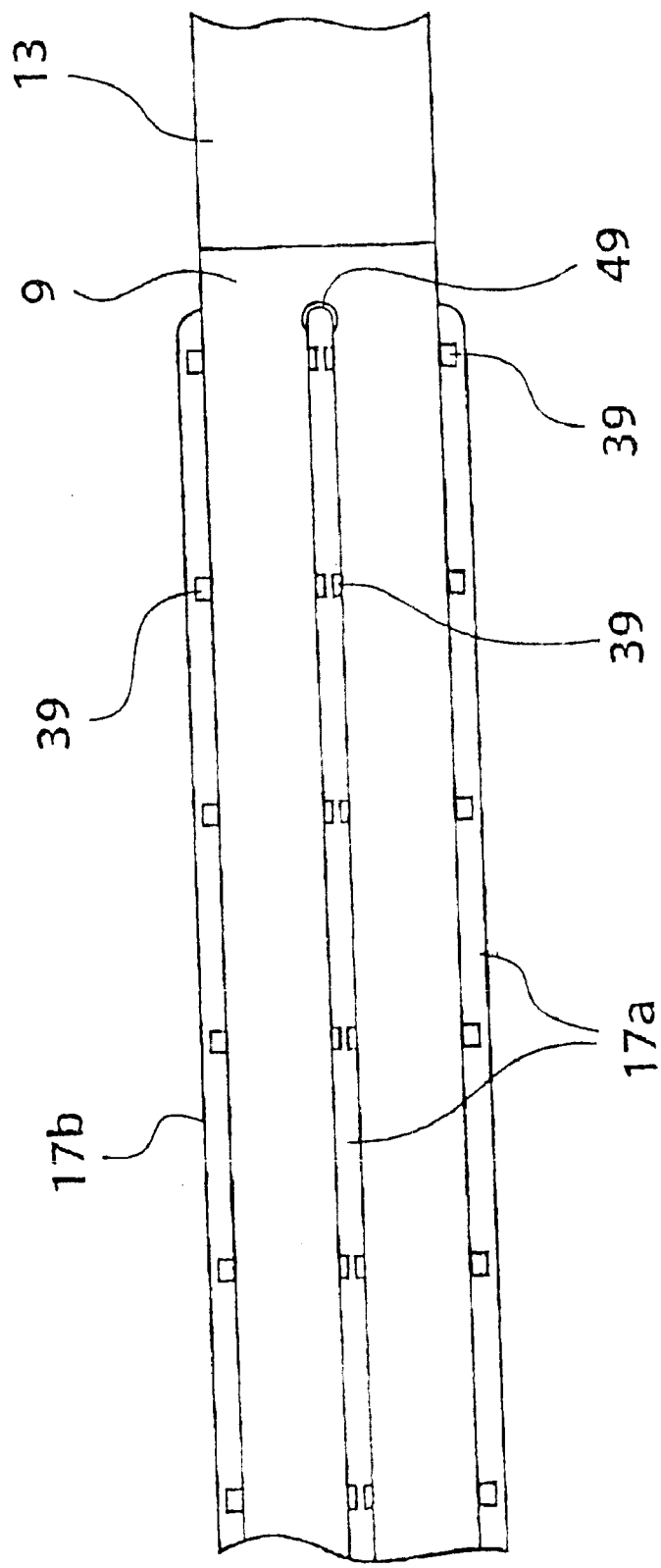
FIG. 5 shows a side view of a portion around the distal end of the flexible section of the insertion tube of the colonoscope according to the invention.
Figure 6:
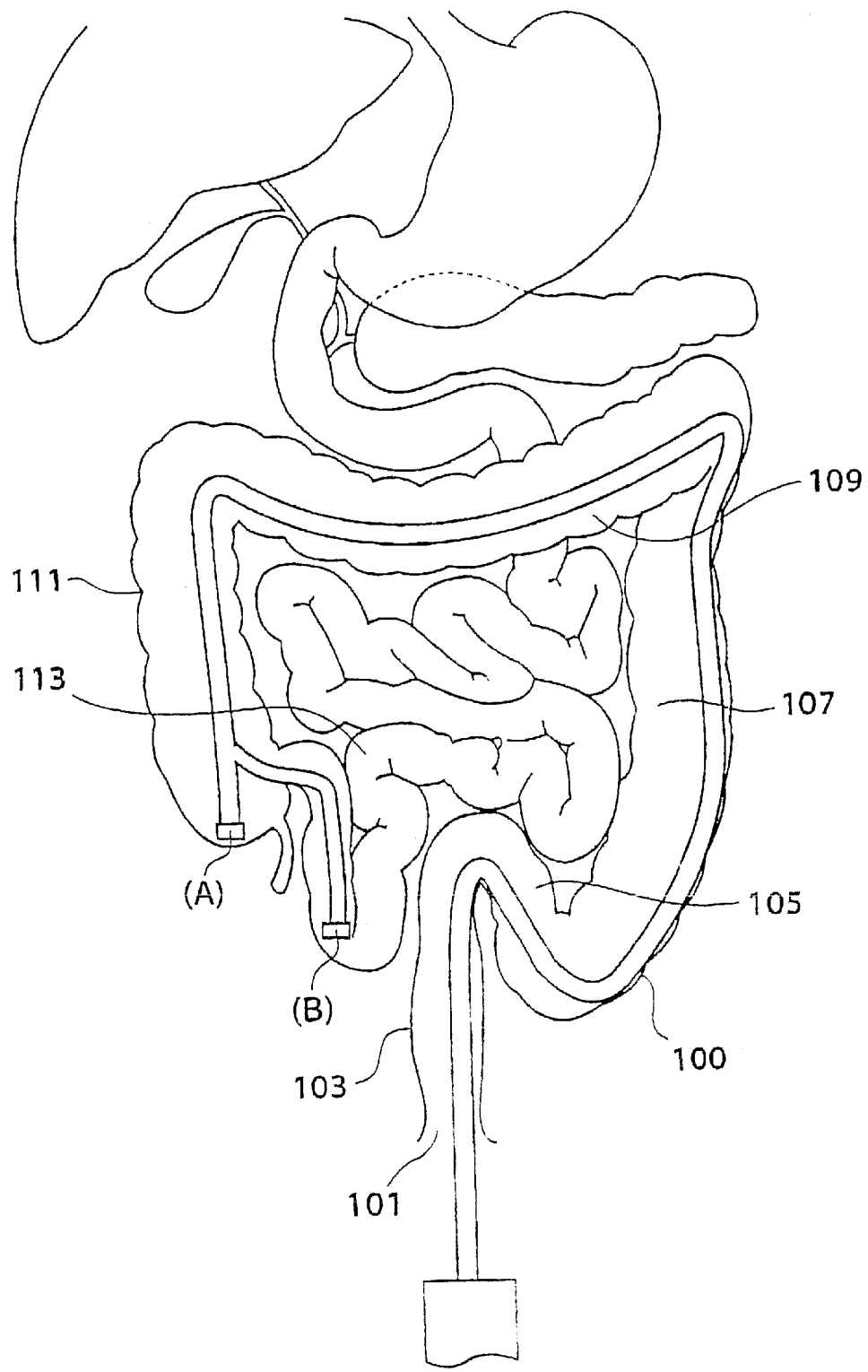
FIG. 6 is a drawing schematically showing an insertion path of a conventional colonoscope.

FIG. 5 shows a side view of a portion around the distal end of the flexible section of the insertion tube of the colonoscope according to the invention.

At the distal section 11 of the insertion tube 9, as shown in FIG. 4, an image receiving window 19, two light projecting windows 21, a suction and forceps opening 23, and an air-water nozzle 25 are provided. The image-receiving window 19, equipped with an objective lens when the observation device is a fiberscope, or an image pick-up device, such as a CCD, when it is an electronic scope, receives an image from the distal end surface thereof. The received image is transmitted to the operation unit 7 by an image guide of the fiberscope or lead wire of the electronic scope, which is inserted in the insertion tube 9, and then transmitted through a universal cord 27 to a display and the like to be displayed. A light guide, such as an optical fiber, is inserted in the bore of each of the light projecting windows 21, runs through the operation unit 7 and is connected to a light source outside via the universal cord 27. The light source projects light from the distal end surface of the light guide.

The suction and forceps opening 23 is connected to a forceps insertion opening 29 of the operation unit 7 and a forceps 31 is inserted therein. The tip ends of the forceps 31, protruding from the distal end of the insertion tube 9, are manipulated at the proximal part of the forceps 31 to perform procedures such as treating a lesion of a patient or collecting a tissue from a patient.

The bore of the air-water nozzle 25 is a water-air supply channel, and air or a cleaning solution is injected through the air-water nozzle 25 by manipulating the air-water supply button 33 of the operation unit 7. Through the suction and forceps opening 23, body fluid or cleaning solution remaining in the colon is sucked out and discharged to outside of the patient's body. This operation is carried out by manipulating a suction control button 35 of the operation unit 7.

The bending section 13 of the insertion tube 9 is able to bend upwardly and downwardly, to right and left, and obliquely by manipulating a control latch 37 provided at the operation unit 7.

A plurality of endless belts 17 are longitudinally arranged on the outside surface of the flexible section 15 of the insertion tube 9. The diameter of the flexible section 15 is preferably 5 to 30 mm; 16 mm is most preferable. A larger number of endless belts is preferable, because the larger the number of endless belts, the higher the self-propelling performance of the colonoscope. As shown in FIG. 3, the outside portion 17a of the endless belt 17 is supported by a guide hook 39 provided at the outside surface of the insertion tube 9. The inside portion 17b of the endless belt 17 passes through a guide pipe 41 in the tube. Each of the guide hooks 39, having a circular-arc-shaped cross section whose interior angle thereof is over 180 degrees, is longitudinally mounted at the flexible section 15 so that a portion of each of the endless belts 17 exposed from each of the guide hooks 39 will be positioned radially and outwardly. Accordingly, the outer surfaces of the endless belt 17 supported by the guide hooks 39 are exposed to the outside of the guide hook 39 so that the endless belts can maintain a sufficient contact area with the inner wall of the colon when inserted into the colon. Even when the flexible section 15 is severely bent, the endless belts 17 will not come off the guide hooks 39.

Each of the endless belts 17 is made of a flexible and strong material such as, for instance, carbon fiber or resin, and the shape of the section thereof may be a circle whose diameter is 1 to 3 mm or flat like a belt with a width of 1 to 3 mm. The length of the endless belt is described later. It is preferable for the back surface of each of the endless belts 17 to be coated with a material having a high friction resistance or to have a rack so as to rotate synchronously with a drive roller 43, shown in FIG. 2.

And, when cleaning the colonoscope, it is necessary to remove the endless belt 17 from the insertion tube 9, so that it is constructed to be separable one way and reconnectable.

Next, referring now to FIG. 2, the construction of the proximal part of the guide pipe 41 and the driving unit 5 of the endless belt will be explained.

The proximal part of the guide pipe 41 is connected to a guide pipe opening 45 provided at the side surface of the driving unit casing 3. The driving unit casing 3 is larger than the insertion tube 9 in diameter. The guide pipe 41 comprises a inclined section 41a, extending diagonally from the guide pipe opening 45 to the insertion tube 9, and a guide section 41c, which extends straight in the insertion tube 9, running from the inclined section 41a to a bending section 41b.

The drive roller 43, pinching the endless belt 17, is mounted outside of the proximal end of the guide pipe 41 in the driving unit casing 3. The endless belt 17 penetrates the side wall of the guide pipe 41 at the inclined section 41a of the guide pipe 41. That is, the exterior portion 17a of the endless belt 17 runs from the outside surface of the insertion tube 9 into the guide section 47, then extends toward the proximal end crossing holes formed at the two side walls of the inclined section 41a and is wound up and held by the drive roller 43. On the other hand, the interior portion 17b of the endless belt 17 penetrates the side wall of the guide pipe 41 at the inside of the inclined section 41a and runs into the guide pipe 41, and, via the inside of the pipe 41, to a guide hole 49 (as shown in FIG. 5) provided near the distal end of the flexible section 15 of the insertion tube 9.

The guide hole 49, as shown in FIG. 5, is preferably positioned at 0 to 10 cm from the distal end of the flexible section 15. This is because the greater the surface where the inside wall of the colon is in contact with the outside portion 17a of the endless belt 17, the higher the self-propelling performance of the self-propelled colonoscope.

On the other hand, the distal section of the insertion tube 9, inserted into the colon, advances from the sigmoid colon to the ileum, and through the descending colon, the transverse colon and the ascending colon, as mentioned above. The diameter of the flexible section is about 16 mm. When the distal end of the colonoscope advances into the colon while bending, the inner circle length and the outer circle length of the inserted flexible section 15 become different. When the distal end of the insertion tube reaches the ileum, and the flexible section 15 with a diameter of 16 mm turns around 360 degrees, the outer circle length is 3.12% longer than the straight length.

Accordingly, it is necessary to set the length of the endless belt 17, arranged on the surface of the flexible section 15, to allow for differences between the inner circle length and the outer circle length. For this reason, the length of the endless belt is made to be 102 to 104% of the length of such belt when it tightly turns around from the guide hole near the tip of the flexible section 15 to the same guide hole 49, through the driving unit, while the flexible section 15 is kept straight. Since the length of the endless belt 17 is set as above, the endless belt 17 can sufficiently follow the bend of the flexible section 15. Therefore, it is possible to make the colonoscope advance into the colon stably.

The drive roller 43 comprises a pulley 43b, wound by the endless belt 17, and a bevel gear 43a, connected to the same shaft as the pulley 43b. The endless belt 17 and the pulley 43b are engaged together by friction or a rack function. A bevel gear 50, being engaged with the bevel gear 43a, is so arranged to orthogonalize to the bevel gear 43a. A spur gear 53 is fixed to the proximal part of a gear shaft 51 of the bevel gear 50. The spur gear 53 is engaged with a large spur gear 59 fixed to a motor shaft 57 of a motor 55. Consequently, when the motor shaft 57 revolves when driven by the motor 55, the bevel gear 43a will revolve, via the large spur gear 59, the spur gear 53, and the bevel gear 50, and accordingly the pulley 43b will revolve together.

On the circumference of the large spur gear 59, are mounted the same number of drive rollers 43, bevel gears 50, gear shafts 51, and spur gears 53, as endless belts 17. Incidentally, at that time, a gear 63 may be mounted between the large spur gear 59 and the spur gear 53 in order to drive each of the endless belts 17 in the same direction.

The motor 55, the large spur gear 59, the spur gear 53, the gear shaft 51, the bevel gear 50, and the drive roller 43 are mounted in the driving unit casing 31 provided at the proximal end side of the guide pipe opening 45. On the side surface of the driving unit casing 3, a cleaning opening 60 is formed. The opening 60 is provided with a lid 61, shown in FIG. 1, and can be opened or closed. The opening 60 may be opened to access the space containing the large spur gear 59, the spur gear 53, the gear shaft 51, the bevel gear 50, and the drive roller 43. A space containing the large spur gear 59, the spur gear 53, the gear shaft 51, the bevel gear 50, and the drive roller 43, and a space provided with the motor 55 are water-tightly isolated.

When the motor 55 is driven to rotate the pulley 43b counterclockwise, the exterior portion of endless belt 17 engaged with the pulley 43b will rotate to the left. At this time, if the outer surface of the endless belt 17 is in contact with the inside wall of the colon, the insertion tube 9 will be fed forward to the right as illustrated in FIG. 2 by friction between the endless belt 17 and the inside wall of the colon. The insertion tube 9 moves back by rotating the motor 55 clockwise.

Cleaning of the self-propelled colonoscope 1 is carried out as mentioned below.

First, the endless belt 17 is separated one way and removed from the insertion tube 9. A cleaning brush is inserted from the guide pipe opening 45, provided at the driving unit casing 3, and the brush is moved in and out of each guide pipe 41 to remove body fluid and waste attached to the inner surface of the guide pipe 41.

Next, the lid 61 of the driving unit casing 3 is opened, and then the insertion tube 9, the operation unit 7 and a bottom part of the driving unit casing 3 are immersed into a cleaning tank filled with a cleaning solution. At this time, the colonoscope should be supported such that the drive roller 43 in the driving casing 3 is immersed in the cleaning solution and the motor 55 is positioned above the solution. If a part beyond the gear shaft 51 is immersed in the solution, the solution flows from the opening window 60 to the driving unit 5 and further to the guide pipe 41 and the inside of the guide section 47. The drive roller 43 is immersed also. Accordingly, all surfaces of the insertion tube 5, the inside and outside of the guide pipe 41 which extend from the guide pipe opening 45 to the guide hole 49, the guide section 47 and the drive roller 43 are immersed in the cleaning solution to be cleaned.

What is claimed is:

1. A self-propelled colonoscope, comprising an insertion tube having a distal section, a bending section, and a flexible section having an outer surface, a throughbore and a tip;

said distal section being provided with a lattice of the fiber of an image sensor element or an image-guide and a lattice of the fiber is of a light-guide;

said flexible section being provided with an endless belt;

a driving unit mounted at a driving casing for driving the endless belt;

said endless belt extending within said throughbore from the driving unit to a guide hole near the tip of the flexible section, and then extending on the outer surface of the flexible section through the guide hole back to the driving unit, whereby the colonoscope will be self-propelled into a colon by driving said endless belt;

wherein the length of said endless belt is 102 to 104% of an imaginary endless belt fully tensioned and held at one end by the guide hole near the tip of said flexible section and at another end by the driving unit, while the insertion tube is maintained straight.

2. A self-propelled colonoscope comprising:

a control part, and an insertion tube which comprises a distal section, a bending section, and a flexible section having a throughbore and an outer surface comprising a plurality of arc-shaped guide hooks;

said bending section extending between said flexible section and said distal section, and said flexible section extending between said control part and said bending section;

drive means located at said control part for driving at least two endless belts;

each endless belt extending between said control part and a respective guide hole of a plurality of guide holes;

each guide hole extending through said flexible section from said outer surface to said throughbore;

each endless belt extending within said flexible section in said throughbore from said control part to a respective guide hole and then extending external of said flexible section along said outer surface through respective guide hooks of said plurality of guide hooks from a respective guide hole back to said control part;

wherein the length of the each endless belt is equal to about 102% to 104% of an imaginary endless belt fully tensioned and held at one end by a respective guide hole near the tip of said flexible section and at another end by the driving unit, while the flexible section is held straight.

3. The self-propelled colonoscope according to claim 2, wherein each guide hole is positioned from 0 to 10 centimeters from the tip of said flexible section.

4. The self-propelled colonoscope according to claim 2, wherein the arc shape of each guide hook is greater than 180°.

* * * * *